US00PP11773P2

(12) United States Plant Patent
Rother

(10) Patent No.: US PP11,773 P2
(45) Date of Patent: Feb. 13, 2001

(54) ARGYRANTHEMUM PLANT NAMED 'MIDAS GOLD'

(76) Inventor: Reinhard W. Rother, 56 Emerald Monbulk Road, Emerald, Victoria, 3782 (AU)

( * ) Notice: Under 35 U.S.C. 154(b), the term of this patent shall be extended for 0 days.

(21) Appl. No.: 09/263,151

(22) Filed: Mar. 5, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Marguerite Daisy plant named Midas Gold, characterized by its rounded, outwardly spreading and mounding plant habit; freely branching, dense and bushy plants; very narrow, deeply divided, lacy, fern-like leaves; freely flowering with numerous inflorescences per plant held beyond the foliage; large single-type inflorescences; yellow ray florets and distinct brownish red-tipped immature disc florets which give an "bull's eye" appearance to the inflorescence; and high temperature and humidity tolerance.

1 Drawing Sheet

BACKGROUND OF THE INVENTION

The present invention relates to a new and distinct cultivar of Marguerite Daisy plant, botanically known as *Argyranthemum frutescens* and referred to by the cultivar name Midas Gold.

The new cultivar is a product of a planned breeding program conducted by the Inventor in Emerald, Victoria, Australia.

The new cultivar originated from a cross made by the Inventor in 1994 of an unidentified selection of *Argyranthemum frutescens,* as the male or pollen parent, with an unidentified selection of *Argyranthemum frutescens* as the female or seed parent. The cultivar Midas Gold was discovered and selected by the Inventor as a flowering plant within the progeny of the stated cross in a controlled environment in Emerald, Victoria, Australia.

Asexual propagation of the new cultivar by terminal cuttings in Emerald, Victoria, Australia, has shown that the unique features of this new Marguerite Daisy are stable and are reproduced true to type in successive propagations.

SUMMARY OF THE INVENTION

The new Marguerite Daisy has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Midas Gold' which distinguish 'Midas Gold' as a new and distinct cultivar:

1. Rounded, outwardly spreading and mounding plant habit; vigorous; freely branching, dense and bushy plants.
2. Very narrow, deeply divided, lacy, fern-like leaves.
3. Freely flowering with numerous inflorescences per plant held beyond the foliage.
4. Large single-type inflorescences.
5. Yellow ray florets and distinct brownish red-tipped immature disc florets which give an "bull's eye" appearance to the inflorescence.
6. High temperature and humidity tolerance.

Plants of the new Marguerite Daisy can be compared to plants of the cultivar Lemon Delight (U.S. Plant patent application Ser. No. 09/263,150). In side-by-side comparisons conducted in Emerald, Victoria, Australia, plants of the new Marguerite Daisy are different from plants of the cultivar Lemon Delight in ray and disc floret color and leaf shape.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of two typical plants of 'Midas Gold' in a 25-cm container.

The photograph at the bottom of the sheet comprises close-up views of developing inflorescences (top) and mature and young leaves (bottom). Floret and foliage colors in the photographs may appear different from the actual colors due to light reflectance.

DETAILED BOTANICAL DESCRIPTION

The following observations, measurements and values describe a 25-cm container of two plants of the new Marguerite Daisy grown in Bonsall, Calif., in full sun with day temperatures ranging from 18 to 35° C. and night temperatures ranging from 13 to 18° C.

Color references are made to The Royal Horticultural Society Colour Chart except where general terms of ordinary dictionary significance are used.

Botanical classification: *Argyranthemum frutescens* cultivar Midas Gold.

Parentage:

*Male or pollen parent.*—Unidentified selection of *Argyranthemum frutescens.*

*Female or seed parent.*—Unidentified selection of *Argyranthemum frutescens.*

Propagation:

*Type.*—Terminal cuttings.

*Time to initiate roots.*—About 15 to 18 days at a temperatures of 22 to 25° C.

*Time to develop roots.*—About 30 days at a temperatures of 22 to 25° C.

*Rooting habit.*—Numerous, fine, and freely branching.

Plant description:

*General appearance.*—Rounded, outwardly spreading, bushy and mounding plant habit. Freely branching, dense and full plant habit. Finely pinnatifid foliage. Flexible wiry flower stems hold the inflorescences beyond the foliage; inflorescences occasionally appear to cascade. Appropriate for various sizes and types of containers.

*Crop time.*—About 8 to 12 weeks are required to produce a finished flowering plant in a 10-cm container from a rooted cutting.

*Plant height.*—About 36 cm from soil level to top of inflorescences.

*Plant width.*—About 45 to 60 cm.

*Branching.*—Freely branching; about six to ten primary lateral branches with about four secondary laterals and two or three tertiary laterals.

*Vigor.*—Vigorous.

*Lateral branches.*—Length: About 40 cm. Diameter: About 6 mm. Internode length: About 1 to 1.8 cm. Texture: Glabrous; primary laterals, woody at base.

*Stem color.*—Green, 144A, no anthocyanin.

*Foliage description.*—Arrangement: Alternate, single. Quantity of leaves per lateral branch: Numerous, about 50. Shape: Finely pinnatifid; lacy and fern-like. Apex: Three or four-parted. Base: Attenuate; clasping; sessile. Margin: Seven-lobed; deeply incised; very narrow lobes. Length: About 9 cm. Width: About 3.5 cm. Texture: Glabrous and smooth. Durability to stresses: Good, very durable. Leaves have a waxy cuticle that resists water loss. Color: Young leaves, upper surface: 137B. Young leaves, lower surface: 137C. Mature leaves, upper surface: 137A; 144A towards stem. Mature leaves, lower surface: 137C. Venation, upper surface: 137B. Venation, lower surface: 137C.

Flowering description:

*Flowering habit.*—Inflorescences on wiry and flexible peduncles held beyond the foliage. Flat, single-type composite inflorescence form. Inflorescences form at upper leaf axils. Florets arranged acropetally on a capitulum. Inflorescences last about one week. Inflorescences persistent.

*Quantity of inflorescences.*—Freely flowering; typically about 16 inflorescences and buds per lateral stem; usually about 380 inflorescences and buds per plant.

*Natural flowering season.*—Natural flowering season is spring to early fall. Plants flower continuously during this period.

*Inflorescence size.*—Diameter: About 4.5 cm. Depth (height): About 1.5 cm. Disc diameter: About 1.2 cm.

*Fragrance.*—None.

*Ray florets.*—Aspect: Angled slightly upright with subsequent development, florets tend to reflex. Quantity per inflorescence and arrangement: About 20 ray florets arranged in a double whorl. Shape: Ligulate. Apex: Irregularly three or four-dentate. Base: Attenuate. Margin: Entire. Length, outer florets: About 2.4 cm. Width, outer florets: About 7 mm. Texture: Smooth, soft, satiny. Color: When opening, upper surface: 4C, 4A towards base. When opening, lower surface: 4D. Fully opened, upper surface: 4D, 4B/4C towards base; fading to 4D with subsequent development. Fully opened, lower surface: 4D.

*Disc florets.*—Shape: Tubular; 5-lobed. Quantity per inflorescence: About 152. Disc floret length: About 6 mm. Disc floret width: About 2 mm. Color: Immature: 150C; reddish brown, 178B, at apex. Mature: 178A to golden orange, fading to 1D with subsequent development.

*Phyllaries.*—Quantity per inflorescence and arrangement: About 21 per inflorescence; imbricate in three whorls; tightly pressed to the receptacle. Aspect: Cupped. Shape: Elliptic. Apex: Broadly acute. Margin: Entire, outer edges slightly membranous. Texture: Smooth. Length: About 6 mm. Color: Upper surface: 145A. Lower surface: 138A.

*Peduncle.*—Length, first peduncle: About 5.5 cm. Length, fourth peduncle: About 8 cm. Strength: Wiry, flexible, inflorescences held beyond the foliage and occasionally appear to cascade. Angle: Upright to a 45° angle to the stem. Texture: Smooth. Color: 144A.

*Inflorescence bud.*—Shape: Pointed ovoid. Length: About 1.4 cm. Diameter: About 8 mm. Color: 4B.

*Reproductive structures.*—Androecium: Stamens: About five. Anther shape: Oblong. Anther size: Less than 1 mm. Anther color: 1C. Pollen amount: None observed. Gynoecium: Pistil number: One per floret. Pistil length: About 5 mm. Style length: About 3.5 mm. Style color: 2C. Stigma shape: Bilobate. Stigma color: 2A. Ovary color: 2D.

*Seed development.*—Seed production has not been observed.

Disease resistance: Resistance to pathogens common to Argyranthemum has not been observed.

Weather tolerance: Plants of the new Marguerite Daisy have demonstrated good tolerance to high temperature and high humidity conditions.

It is claimed:

1. A new and distinct Marguerite Daisy plant named 'Midas Gold', as illustrated and described.

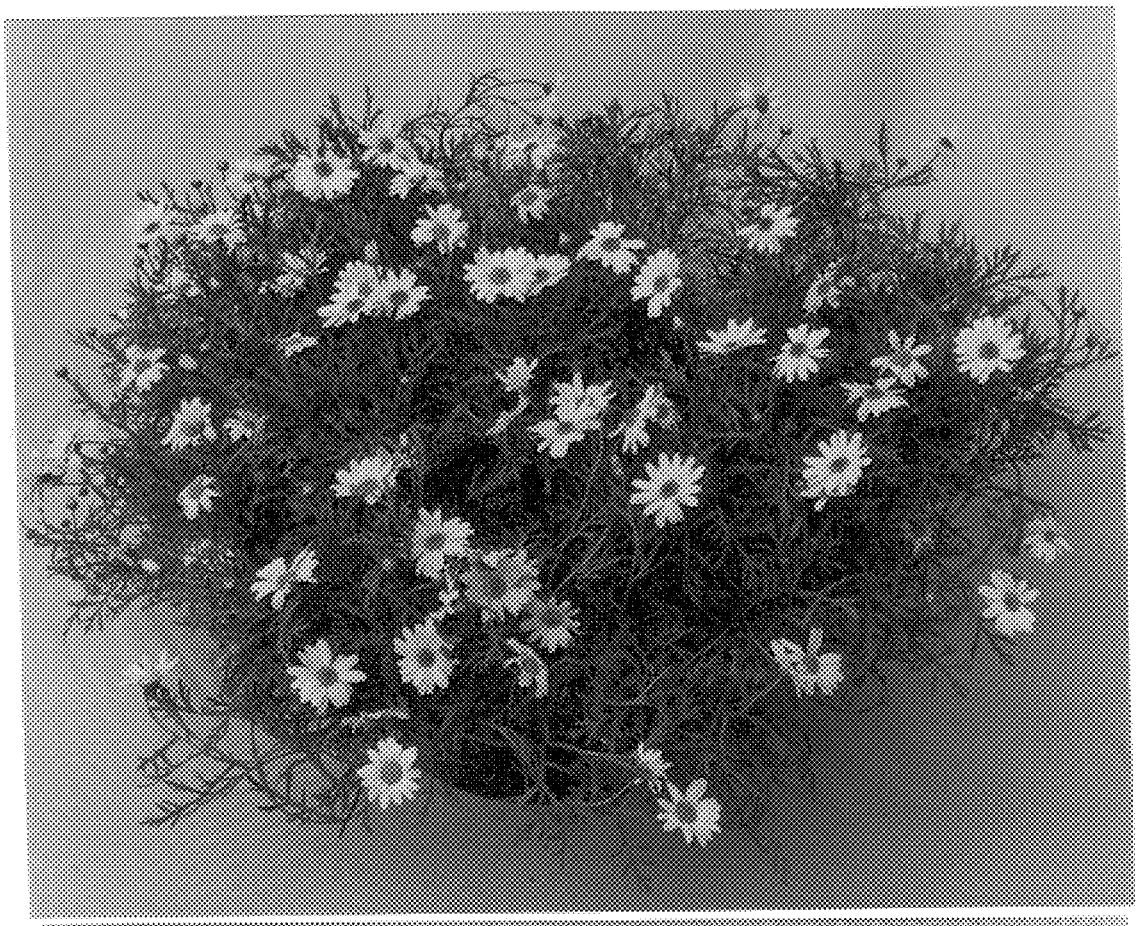
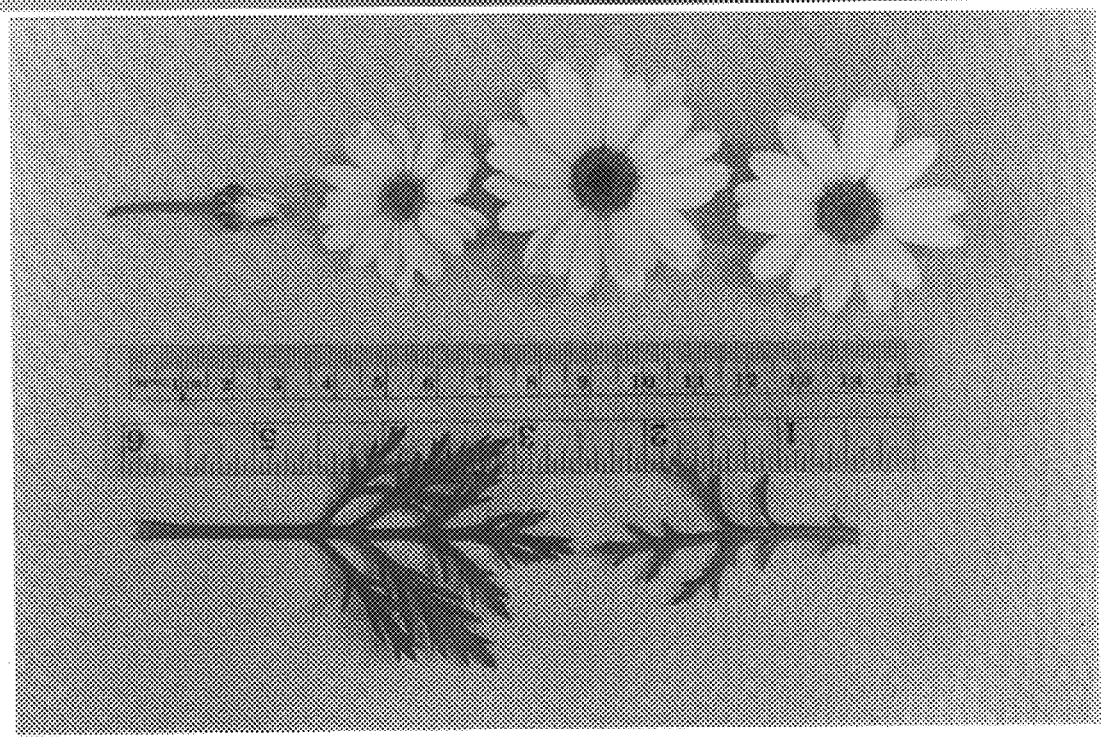

* * * * *